United States Patent
Kobashikawa

(10) Patent No.: US 6,757,914 B1
(45) Date of Patent: Jul. 6, 2004

(54) ADJUSTABLE GLARE SHIELD FOR BRIM CAPS

(76) Inventor: Gary K Kobashikawa, 3460 Maluhia St., Honolulu, HI (US) 96816

( * ) Notice: Subject to any disclaimer, the term of this patent is extended or adjusted under 35 U.S.C. 154(b) by 0 days.

(21) Appl. No.: 10/267,253

(22) Filed: Oct. 9, 2002

(51) Int. Cl.[7] .................................................. A61F 9/00
(52) U.S. Cl. .......................................................... 2/10
(58) Field of Search ......................... 2/10, 12, 209.13; 351/155, 158

(56) References Cited

U.S. PATENT DOCUMENTS

| | | | | |
|---|---|---|---|---|
| 4,541,125 A | * | 9/1985 | Phillips | 2/10 |
| 4,869,586 A | * | 9/1989 | Chung | 351/158 |
| 4,885,808 A | * | 12/1989 | Carpenter | 2/452 |
| 5,422,686 A | * | 6/1995 | Kelman et al. | 351/155 |
| 5,692,234 A | * | 12/1997 | Yuen | 2/10 |
| 5,778,448 A | * | 7/1998 | Maher | 2/10 |
| 6,491,390 B1 | * | 12/2002 | Provost | 351/155 |

* cited by examiner

Primary Examiner—Katherine Moran
(74) Attorney, Agent, or Firm—Michael I Kroll

(57) ABSTRACT

An adjustable glare shield assembly for positioning lenses with respect a users field of vision related to attachment of said glare shield assembly to the underside of a hat or cap brim. Adjustable glare shield consisting of a wire frame having brim clips on both distal ends with a pivotal frame and glass lenses centrally positioned. Pivotal frame comprising of cantilevered arms having apertures for mounting to the wire frame. Stationary washers positioned on exterior sides of cantilevered arms and interior washers positioned on the interior side of cantilevered arms with a spring positioned therebetween pressure against interior washers causing the interior washers to press against cantilevered arms of frame. The pivotal frame and optical members frictionally pivot on wire frame. Said adjustable shield removable or replaceable by user from one hat or cap to another. Frame designable with sun, driving, reading, or other type lenses.

2 Claims, 11 Drawing Sheets

ADJUSTABLE GLARE SHIELD FOR BRIM CAPS

BACKGROUND OF THE INVENTION

FIELD OF THE INVENTION

The present invention relates generally to sun glasses and, more specifically, to an adjustable sun shield for brimmed caps and hats that attaches to the underside of the brim of a cap. The adjustable sun shield of the present invention consists of a wire frame having a clip portion on both distal ends with a pivotal frame and glasses centrally positioned.

Most known types of clip-on sunglasses require the user to remove his or her spectacles in order to attach the auxiliary or clip-on sunglasses thereto. This is usually accomplished by slipping the top portion of the spectacle frame between one or more pairs of fixed resilient clamping prongs or fingers, which are part of the assembly comprising of the flip-up sunglasses. Having to remove ones spectacles to attach the auxiliary sunglasses can be of great inconvenience especially when driving an automobile, fishing, engaging in an athletic event, etc. The attachable flip-up glasses may contain lenses for sun glasses, reading glasses, safety shielding, combinations of function, or other type lenses. The attached lens may be a one-piece lens or two individual (left and right) lenses. Fishermen may want reading glasses readily handy when tying hooks or such activities. Golfers may want sun glasses for wear on the golf course at certain activities as waling the fairway and may not want them when putting. Flip-up type glasses usually require a user to wear other spectacles. Wearing and "at times" removing sum glasses are an inconvenience to the wearer. Wearing a "chain" or other means to hold the sun glasses are also inconvenient when the "chain" or other means is dangling about one's neck and may interfere with the activity at hand.

The present invention solves the problem of inconvenience by offering a solution to access and storage of sunglasses or other type lenses that require ready availability. While other glare shield housing devices may be suitable for the purposes for which they were designed, they would not be as suitable for the purposes of the present invention, as hereinafter described.

The pivotal frame is comprised of cantilevered arms having apertures for mounting to the wire frame. Positioned on the exterior sides of the cantilevered arms are stationary washers. Positioned on the interior side of the cantilevered anus are interior washers having a spring positioned therebetween exerting pressure against the interior washers causing the interior washers to press against the cantilevered arms of the Same. The pivotal frame and optical members frictionally pivot on the wire frame.

The pivotal sun blocking members can be moved from a substantially horizontal non visual impairing position to a vertical vision blocking position or at any point therebetween being held at the desired position by the frictional forces generated by the spring and washers against the frame.

While other glare shield housing devices may be suitable for the purposes for which they were designed, they would not be as suitable for the purposes of the present invention, as hereinafter described.

The present invention is an adjustable glare shield for brimmed caps and hats that attaches to the underside of the brim of a cap. The adjustable glare shield of the present invention consists of a wire frame having a clip portion on both distal ends and a coil spring attached to two inner washers, arm and outer washer. The arm attaches the shield and bridge to the device and allows the shield to move in an upward or downward position. When the shield is engaged in movement the coil spring pushes on the inner and outer washers that hold the arm in place and provide the means for frictionally holding the shield in its adjusted position. The clip portion of the device holds the wire housing to the underside of the brim of a cap, allowing the device to be removed and replaced as desired by the user.

SUMMARY OF THE PRESENT INVENTION

A primary aspect of the present invention is to provide an adjustable glare shield assembly (AGSA) for brimmed caps and hats that attaches to the underside of the brim of a cap.

Another aspect of the present invention is to provide an AGSA for brimmed caps that consists of a wire frame having a clip portion on both distal ends.

Yet another aspect of the present invention is to provide an AGSA for brimmed caps that has a coil spring attached to two inner washers, two clamping arms and two outer washers.

Still yet another aspect of the present invention is to provide an AGSA for brimmed caps such that the clamping arms attach the shield and bridge to the device and allows the shield to move in an upward or downward position.

Another aspect of the present invention is to provide an AGSA for brimmed caps that when the shield is engaged in movement the coil spring pushes on the inner and outer washers that hold the clamping arms in place and provide the means for frictionally holding the shield in its adjusted position.

Yet another aspect of the present invention is to provide an AGSA for brimmed brimmed caps that the clip portion of the device holds the wire housing to the underside of the brim of a cap, allowing the device to be removed and replaced as desired by the user.

Yet another aspect of the present invention is to provide for the use of various type lenses such as sun glass lenses (various shades), reading lenses, night driving lenses, safety lenses, etc.

Other aspects of this invention will appear from the following description and appended claims, reference being made to the accompanying drawings forming a part of this specification wherein like reference characters designate corresponding parts in the several views.

Additional objects of the present invention will appear as the description that proceeds.

The present invention overcomes the shortcomings of prior art by providing an AGSA for brimmed caps and hats that attaches to the underside of the brim of a cap. The AGSA of the present invention consists of a wire frame having a clip portion on both distal ends and a coil spring attached to two inner washers, two clamping arms and two outer washers. The clamping arms attach the shield and bridge to the device and allow the shield to move in an upward or downward position. When the shield is engaged in movement the coil spring pushes on the inner and outer washers that hold the clamping arms in place and provide the means for frictionally holding the shield in its adjusted position. The clip portion of the device holds the wire housing to the underside of the brim of a cap, allowing the device to be removed and replaced as desired by the user.

The present invention employs an adjustable sun shield that attaches to the underside of the brim of a cap or hat. The adjustable sun shield consists of a wire frame having a brim clip portion on both distal ends with a pivotal frame and glasses centrally positioned. The main embodiment of the present invention consists of a pivotal frame is comprised of two cantilevered clamping arms having apertures for mounting to the wire frame. Positioned on the exterior sides of the cantilevered clamping arms are stationary washers. Positioned on the interior side of the cantilevered clamping arms are interior washers having a spring positioned therebetween. The spring exerts pressure against the interior washers causing the interior washers to press against the cantilevered clamping arms of the frame. The pivotal frame and optical members frictionally pivot on the wire frame. An alternate embodiment of the present invention would consist of replacing the spring and pivotable bridge with a pair of slideably interchangeable plates to function in an equivalent manner to that described above in holding the bridge in a fixed position.

The pivotal sun blocking (or other type lenses) members can be moved from a substantially horizontal non-visual impairing position to a vertical vision blocking position or at any point therebetween and are held at the desired position by the frictional forces generated by the spring and washers against the frame.

The clip portion of the device holds the wire housing to the underside of the brim of the cap or hat, thus allowing the device to be removed and placed on another cap or hat as desired by the user. Thus the apparatus of the present invention is portable from one cap (or hat) to another allowing the user flexibility in use with various caps or hats.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

Figure 1:
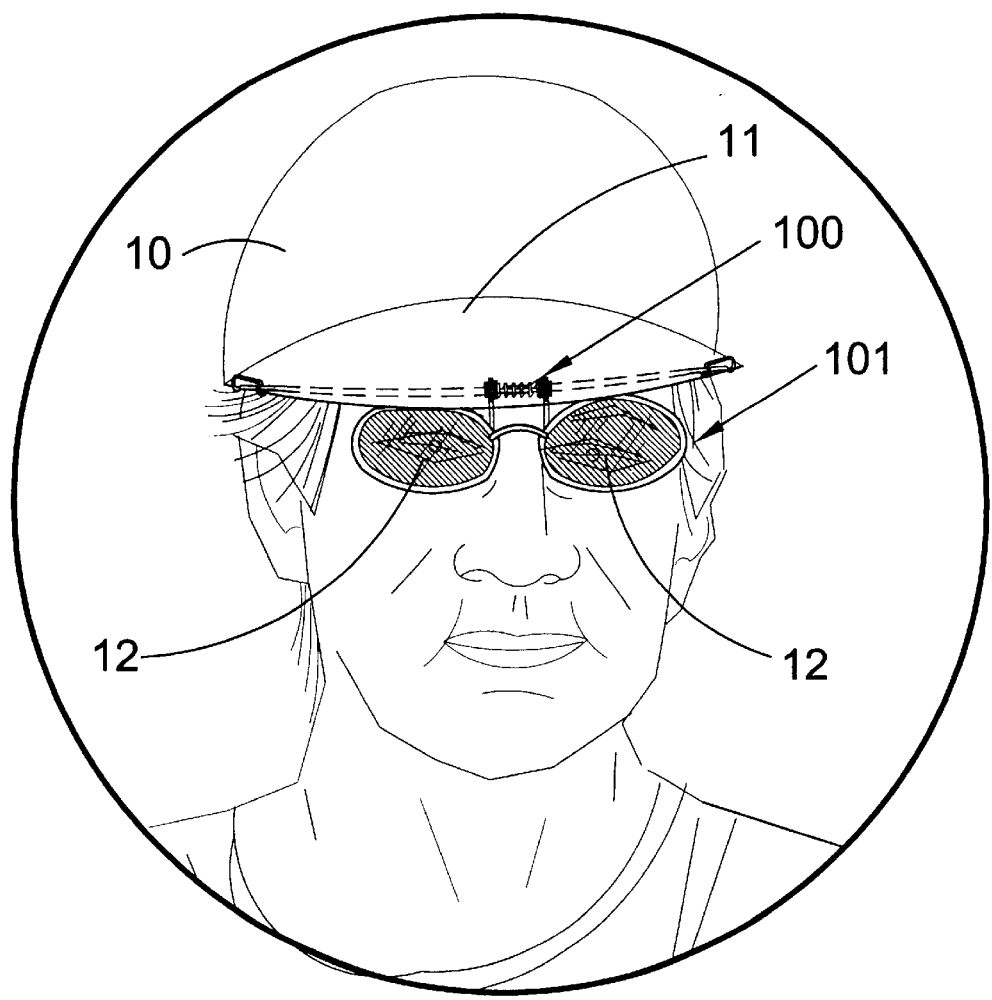
FIG. 1 is an illustrated view of the adjustable glare shield assembly (AGSA) of the present invention in use.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION OF THE REFERENCED NUMERALS

Turning now descriptively to the drawings, in which similar reference characters denote similar elements throughout the several views, the figures illustrate the Adjustable Glare Shield Assembly for Brim Glasses of the present invention. With regard to the reference numerals used, the following numbering is used throughout the various drawing figures.

100 adjustable glare shield assembly (AGSA)
101 moveable shield
10 cap or hat
11 brim
12 sun blocking lens
13 right brim clip
14 left brim clip
15 wire frame
16 left lens shield
17 right lens shield
18 clamping arm
19 bridge
20 coil spring
21 inner washer
22 outer washer
23 swing movement

DETAILED DESCRIPTION OF THE PREFERRED EMBODIMENT

The following discussion describes in detail one embodiment of the invention. This discussion should not be construed, however, as limiting the invention to those particular embodiments, practitioners skilled in the art will recognize numerous other embodiments as well. For definition of the complete scope of the invention, the reader is directed to appended claims.

FIG. 1 is an illustrated view of the apparatus of the present invention in use. Adjustable glare shield assembly (AGSA) 100 is shown attached to the underside of brim 11 of cap 10. AGSA 100 can be removed or replaced, as the user requires. The user can easily move AGSA 100 to other caps or hats as needed. The AGSA 100 can remain on cap 10 when used indoors and cannot get lost or misplaced as easily as other types of glasses. Movable shield 101 can hold a sun blocking lens 12, night driving, reading, safety, or other type lenses. The user does not have to wear spectacles in order to accommodate AGSA 100. Although the lens is shown as two individual lenses, a single one-piece lens can also be employed.

Figure 2:
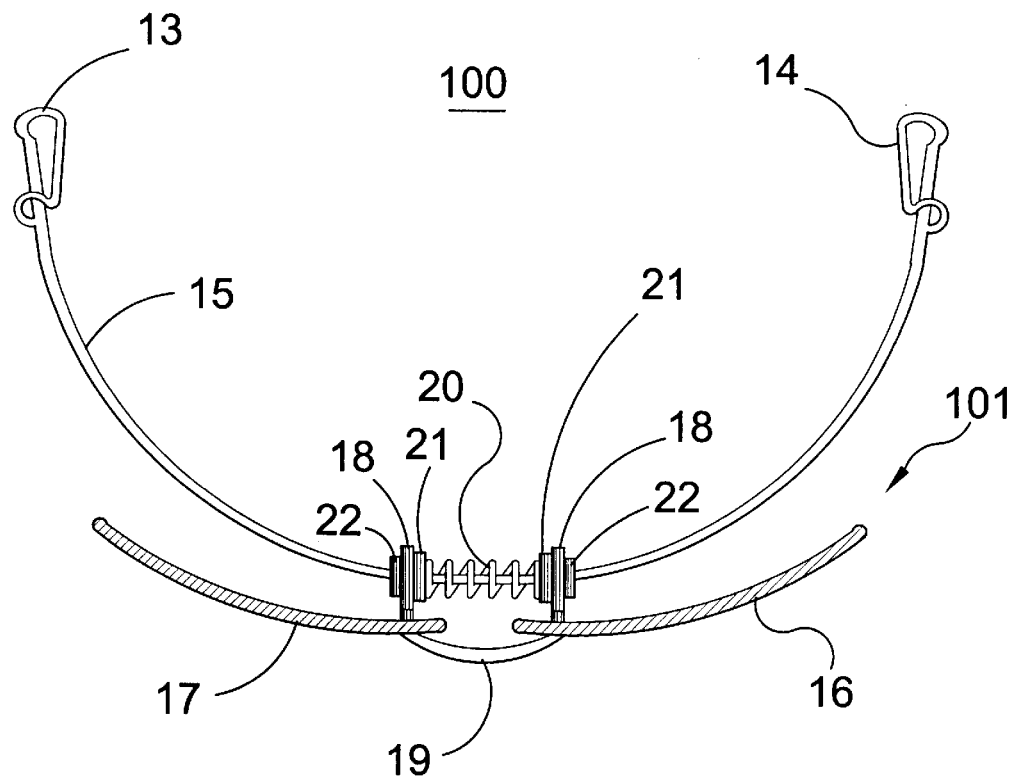
FIG. 2 is a top view of the AGSA of FIG. 1, the preferred embodiment, in the down position.

FIG. 2 is a top view of AGSA 100 with movable shield 101 in the down position. AGSA 100 consists of wire frame 15, right brim clip 13, left brim clip 14, outer washers 22, clamping arms 18, coil spring 20, inner washers 21, and movable shield 101 which, in turn, consists of bridge 19, left lens shield 16, right lens shield 17, and sun blocking lenses 12. It should be noted that sun-blocking lenses 12 could easily be replaced with other type lenses (reading, prescription, etc.) AGSA 100 clips to the underside of the brim of a hat and can be removed or remounted, as the user requires. Bridge 19 allows for attachment of left and right lens shield 16, 17 to itself and to wire frame 15 via clamping arms 18 which are functionally part of bridge 19.

Figure 3:
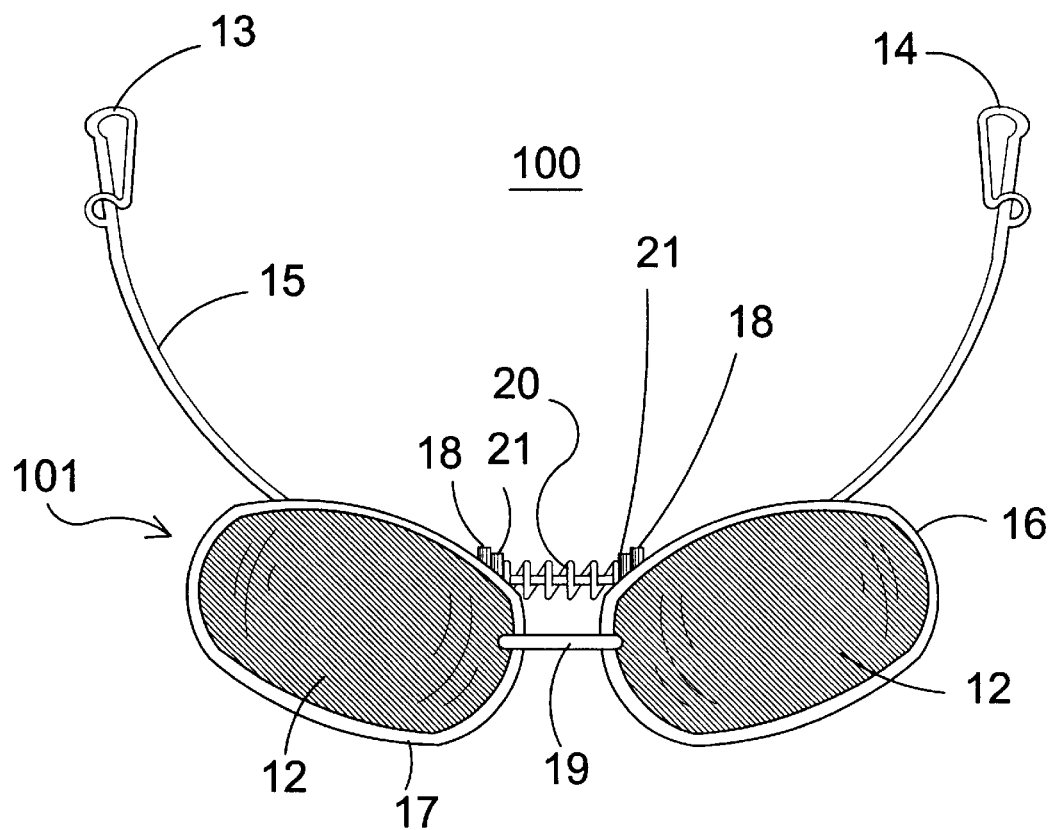
FIG. 3 is a top view of the AGSA of FIG. 1 in the up position.

FIG. 3 is a top view of AGSA 100 with movable shield 101 in the up position. Adjustable glare shield assembly (AGSA) 100 adjusts in an up and downward direction via coil spring 20 pushing on movable inner washers 21 compressing clamping arms 18 between movable inner washers 21 and stationary outer washers 22 (not shown) thereby frictionally holding movable shield 101 in various adjustable positions. FIG. 3 shows movable shield 101 in an up position, that is, somewhat parallel to the brim of a cap. It should be noted that although; left and right lens shield 16, 17 are depicted designed to hold lenses 12, an alternate embodiment of the present invention would be a design whereas lenses 12 directly attach to bridge 19 without a frame type support as offered by lens shields 16, 17.

Figure 4:
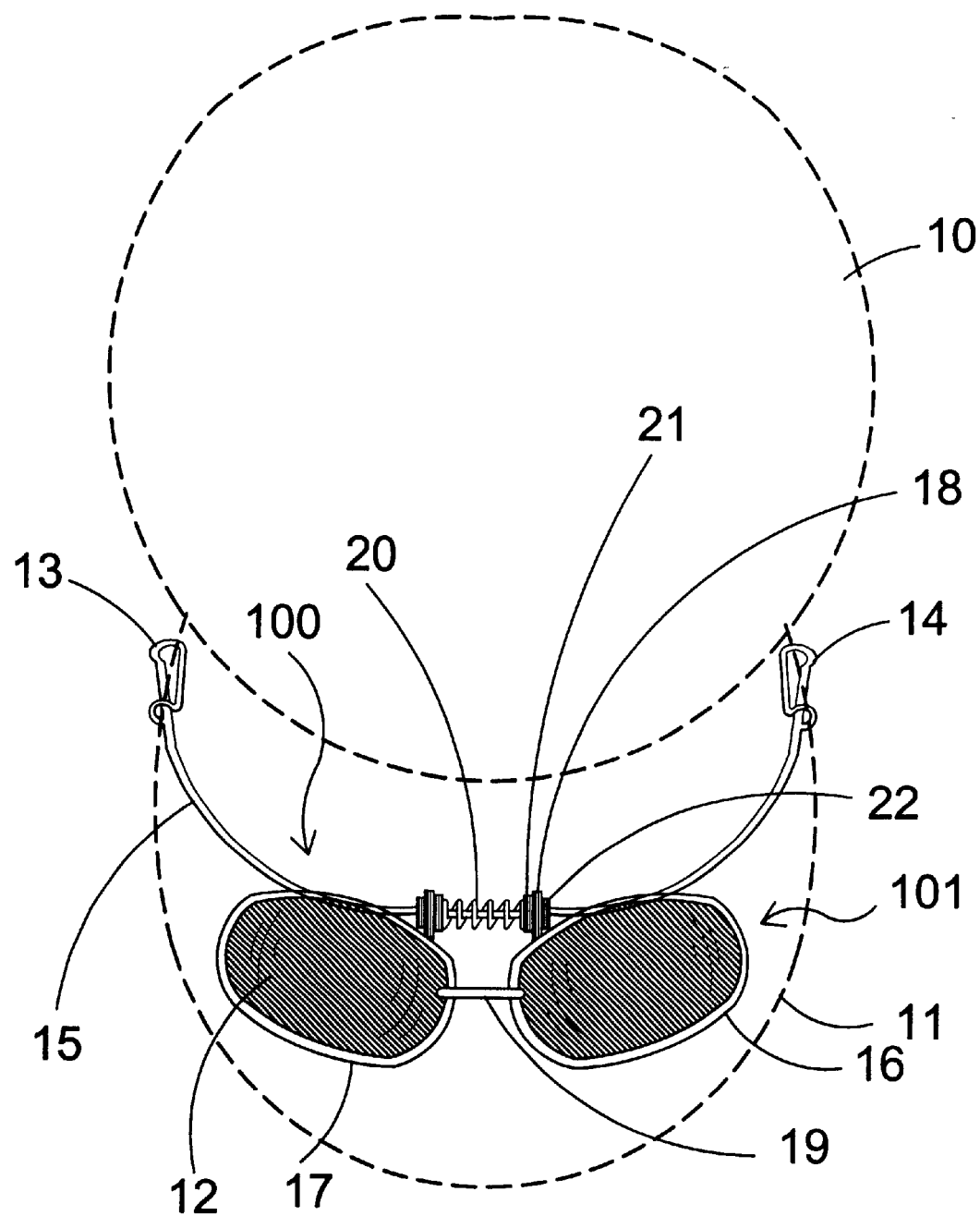
FIG. 4 is a top view of the AGSA of FIG. 1 with shield in the up position within the underside of the brim of a cap or hat.

FIG. 4 is a top view of AGSA 100 with movable shield 101 in the up position within the underside of brim 11 of cap or hat 10. When movable shield 101 is engaged to move in the upward (or downward) position, coil spring 20 pushes on movable inner washers 21 and stationary outer washers 22, that hold the clamping arms 18 in place, and provide a means for frictionally holding the movable shield 101 in the different adjusted positions. FIG. 4 depicts movable shield 101 in a position somewhat parallel to brim 11.

Figure 5:
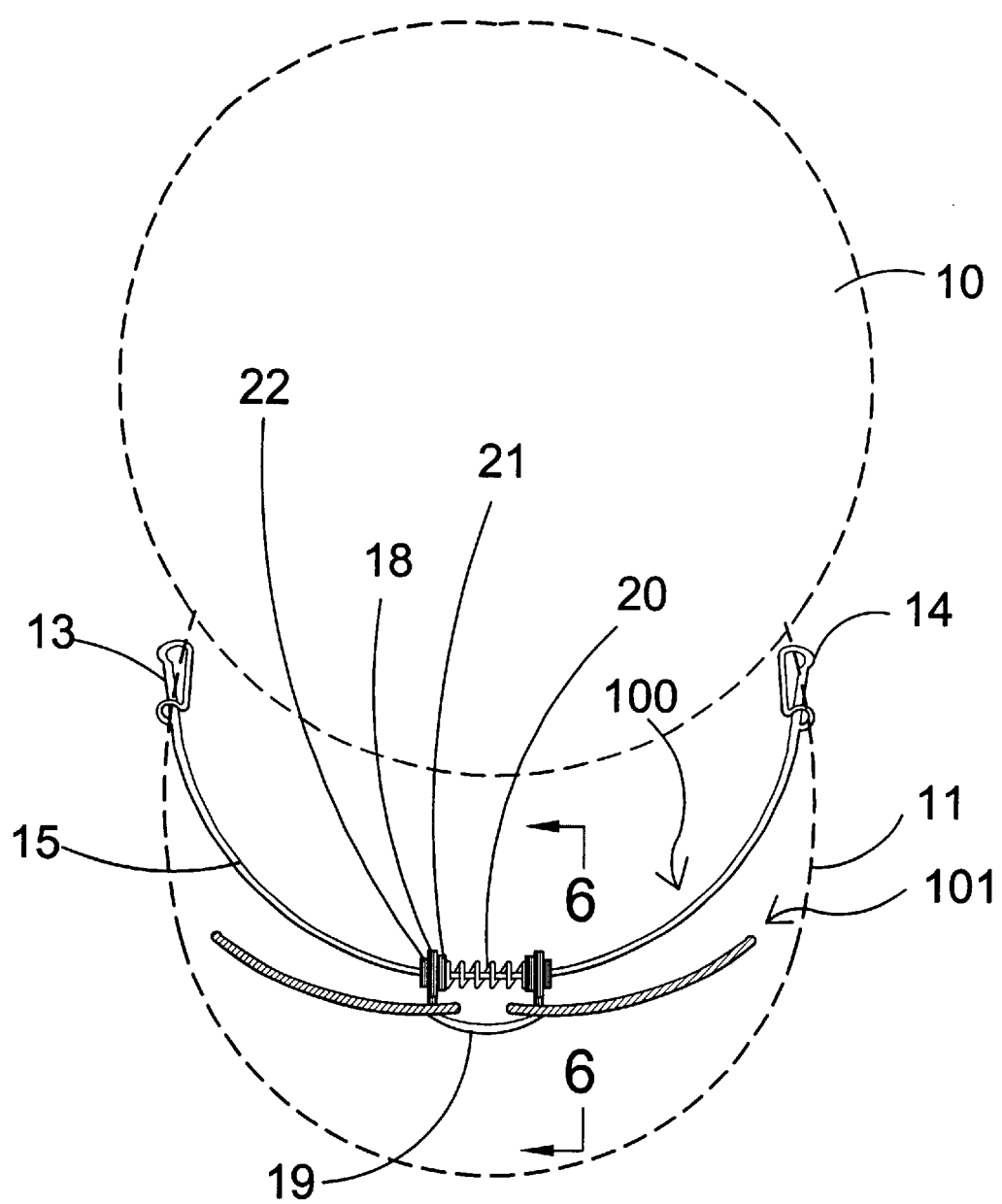
FIG. 5 is a top view of the AGSA of FIG. 1 with movable shield in the down position within the underside of the brim of a cap or hat.

FIG. 5 is a top view of AGSA 100 with movable shield 101 in the down position within the underside of brim 11 of cap or hat 10. In the down position (shown) the movable shield 101 is somewhat perpendicular to brim 11 and parallel to the users face allowing see through vision. As previously stated, coil spring 20 pushes on movable inner washers 21 against clamping arms 18 and stationary outer washers 22 to hold clamping arms 18 in place and provide means for frictionally holding the movable shield 101 in its adjusted position.

Figure 6:
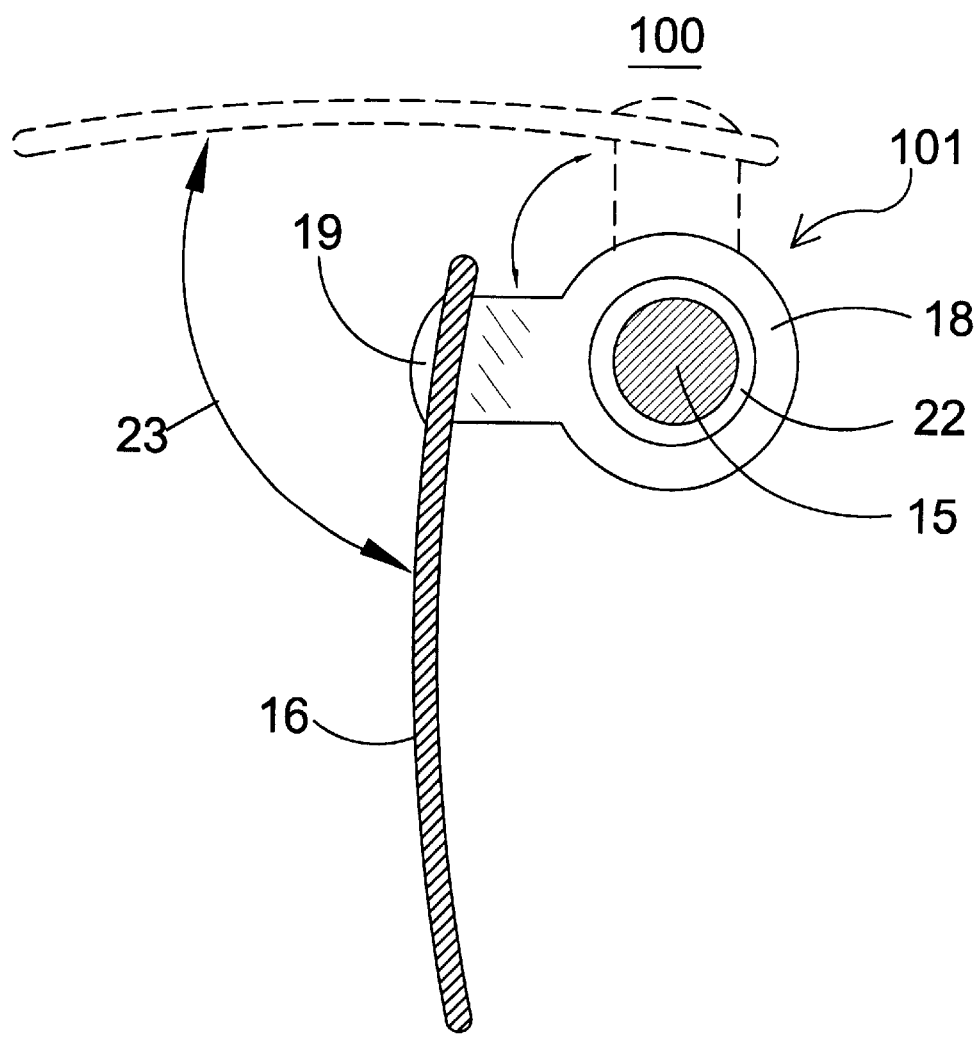
FIG. 6 is a sectional view taken along line 6—6 of FIG. 5 of the AGSA with movable shield illustrated in two positions.

FIG. 6 is a sectional view (sectional view cut 6—6 from FIG. 5) of AGSA 100 with movable shield 101 illustrated in two positions. The sectional view cut of the left side shows wire frame 15, outer washer 22, clamping arm 18 and left lens shield 16. Movable shield 101 is shown in the down position and swing movement 23 depicts the direction of moving from the "down position" shown to the "up position" in which movable shield 101 is shown drawn as a dashed line (indicating the up position).

Figure 7:
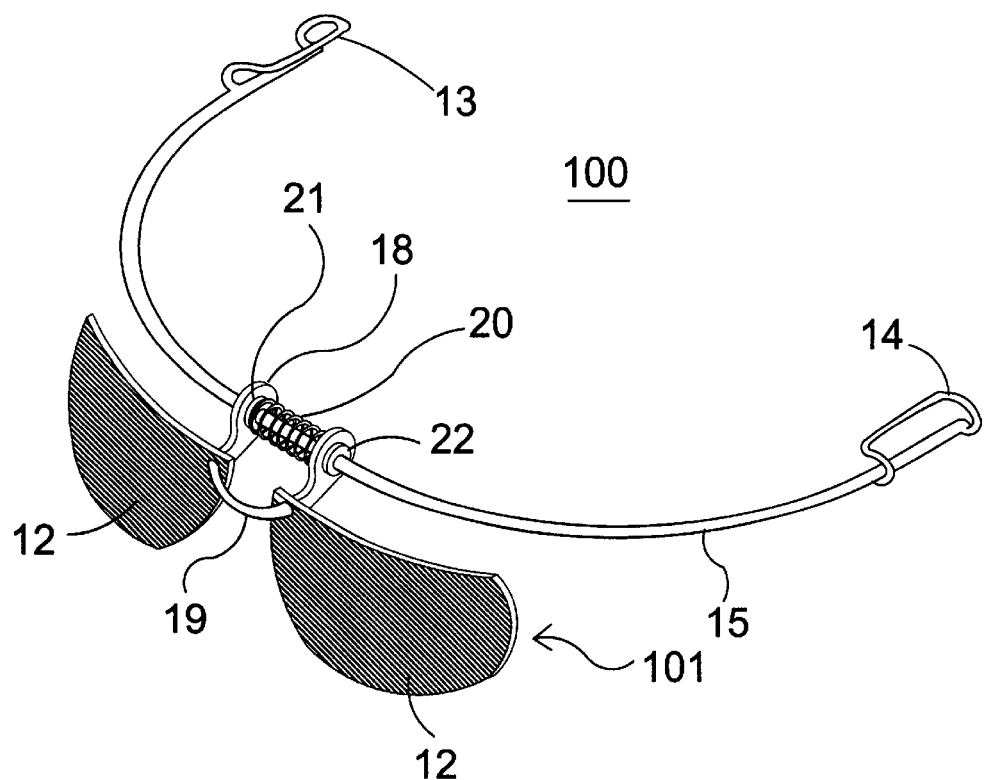
FIG. 7 is a top perspective view of the AGSA of FIG. 1 with shield shown in the down position.

FIG. 7 is a perspective view of the AGSA of the present invention with shield shown in the down position. When movable shield 101 is shown in the down position with coil spring 20 pushing movable inner washers 21 against clamping arms 18 and stationary outer washers 22 to hold the clamping arms 18 in place and provide means for frictionally holding movable shield 101 in its adjusted "down" position. It should be noted that lenses 12 are shown directly attached to bridge 19 without a frame type support as offered by lens shields 16, 17 (see FIG. 3).

Figure 8:
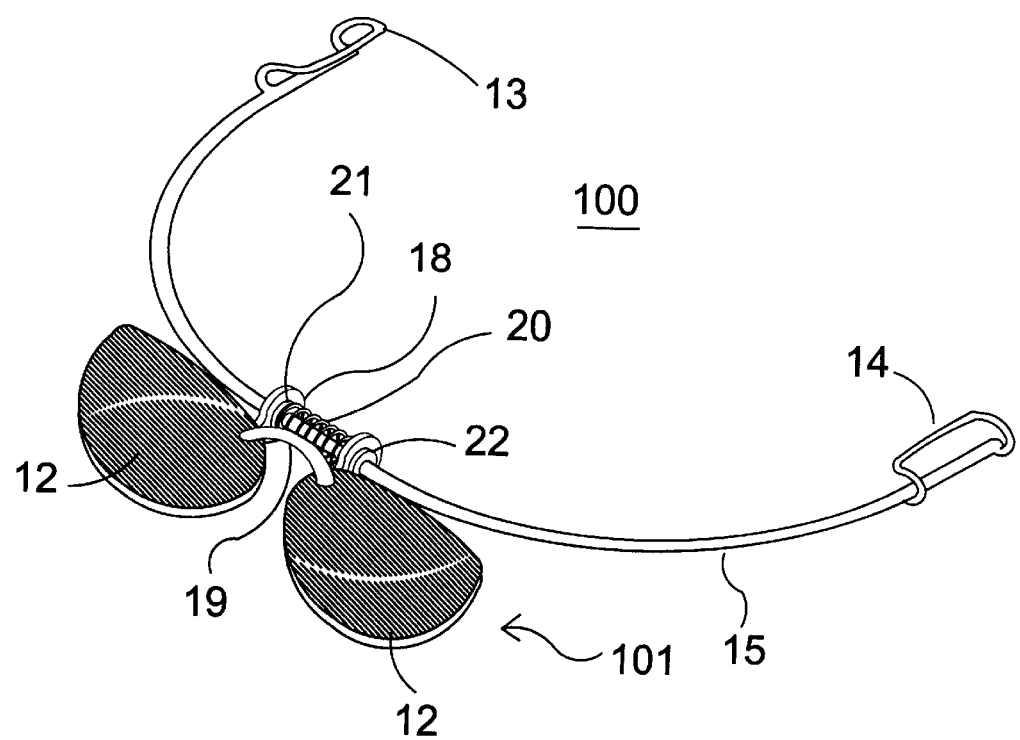
FIG. 8 is a top perspective view of FIG. 1 with shield shown in the up position.

FIG. 8 is a perspective view of AGSA 100 with movable shield 101 shown in the up position. In this position movable shield 101 would be somewhat parallel to a cap or hat brim and out of the users immediate vision field. It again should be noted that lenses 12 are shown directly attached to bridge 19 without a frame type support as offered by lens shields 16, 17 (see FIG. 3).

Figure 9:
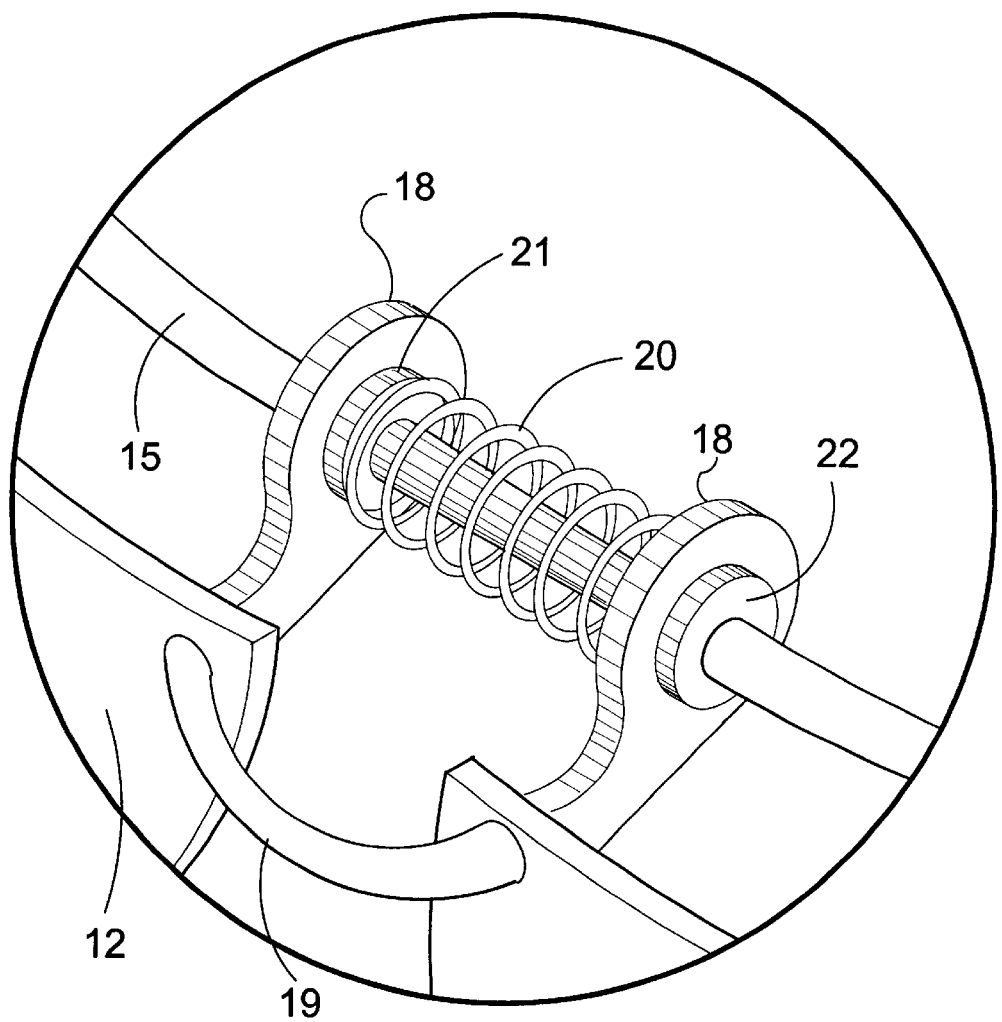
FIG. 9 is a detailed view of the area where the movable shield attaches to the wire frame.

FIG. 9 is a detailed view of the area where movable shield 101 attaches to wire frame 15 showing coil spring 20, clamping arms 18, inner washers 21 (only one shown), outer washers 22 (only one shown), and lens 12 attachment to bridge 19. When the movable shield is engaged to move in an upward or downward position, coil spring 20 pushes on movable inner washers 21 which, in turn, applies pressure to clamping arms 18. This, in turn, applies pressure to stationary outer washers 22 to hold clamping arms 18 in place and thus provide a means for frictionally holding movable shield in its adjusted positions.

Figure 10:
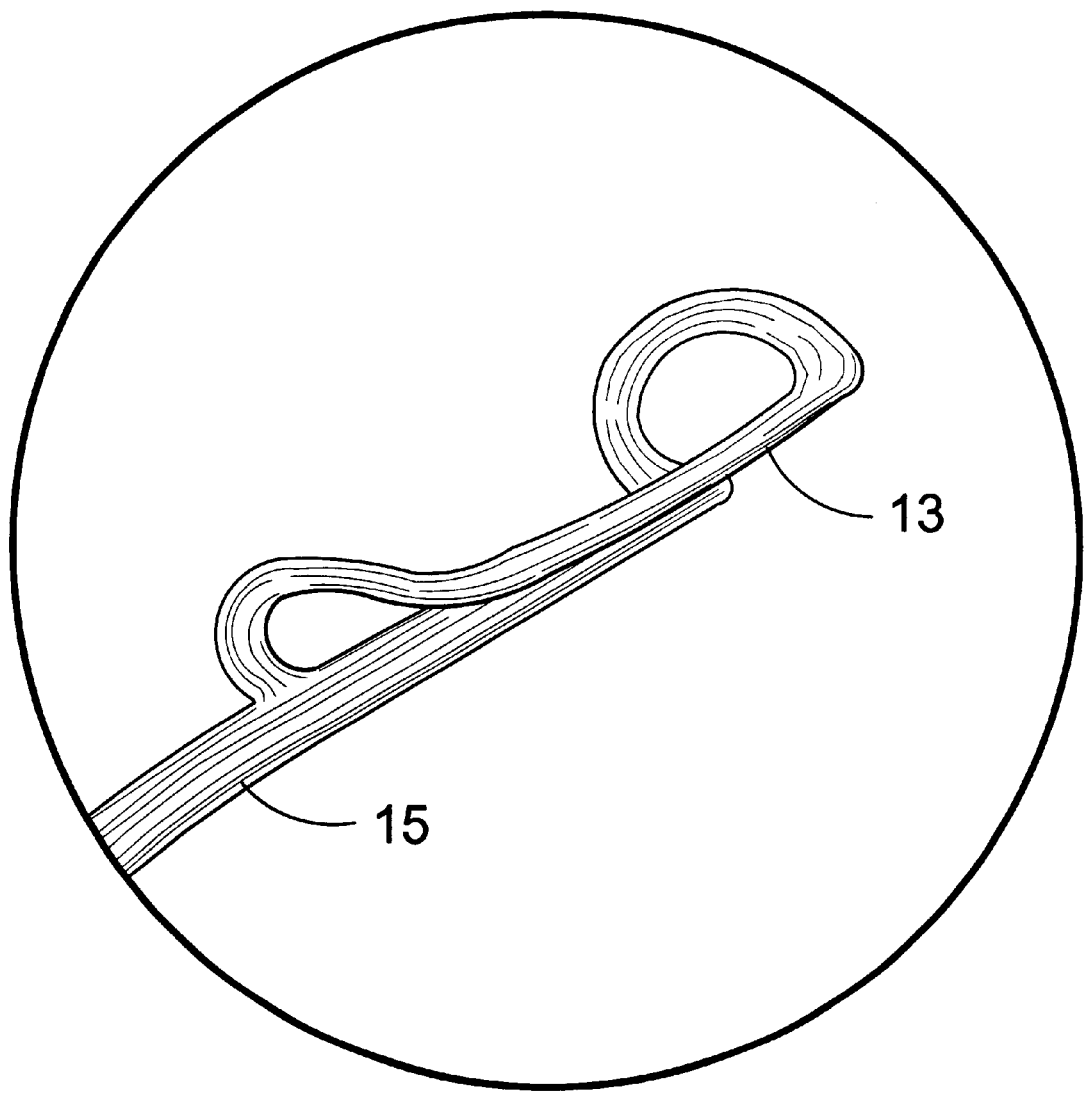
FIG. 10 is a detailed view of the right brim clip portion of the present invention.

FIG. 10 is a detailed view of the right brim clip 13 portion of the present invention. Right brim clip 13 is part of wire frame 15 and attaches to the underside of the brim of a cap or brimmed hat. Right brim clip 13 is a mirror image of left brim clip 14. Each clip holds the AGSA to the brim of the hat firmly and allows the AGSA to be removed and replaced as desired by the user. It should be noted that the brim clip shown is designed to attach the AGSA to the brim of a hat and that other designs variations would be readily apparent to those skilled in the art.

Figure 11:
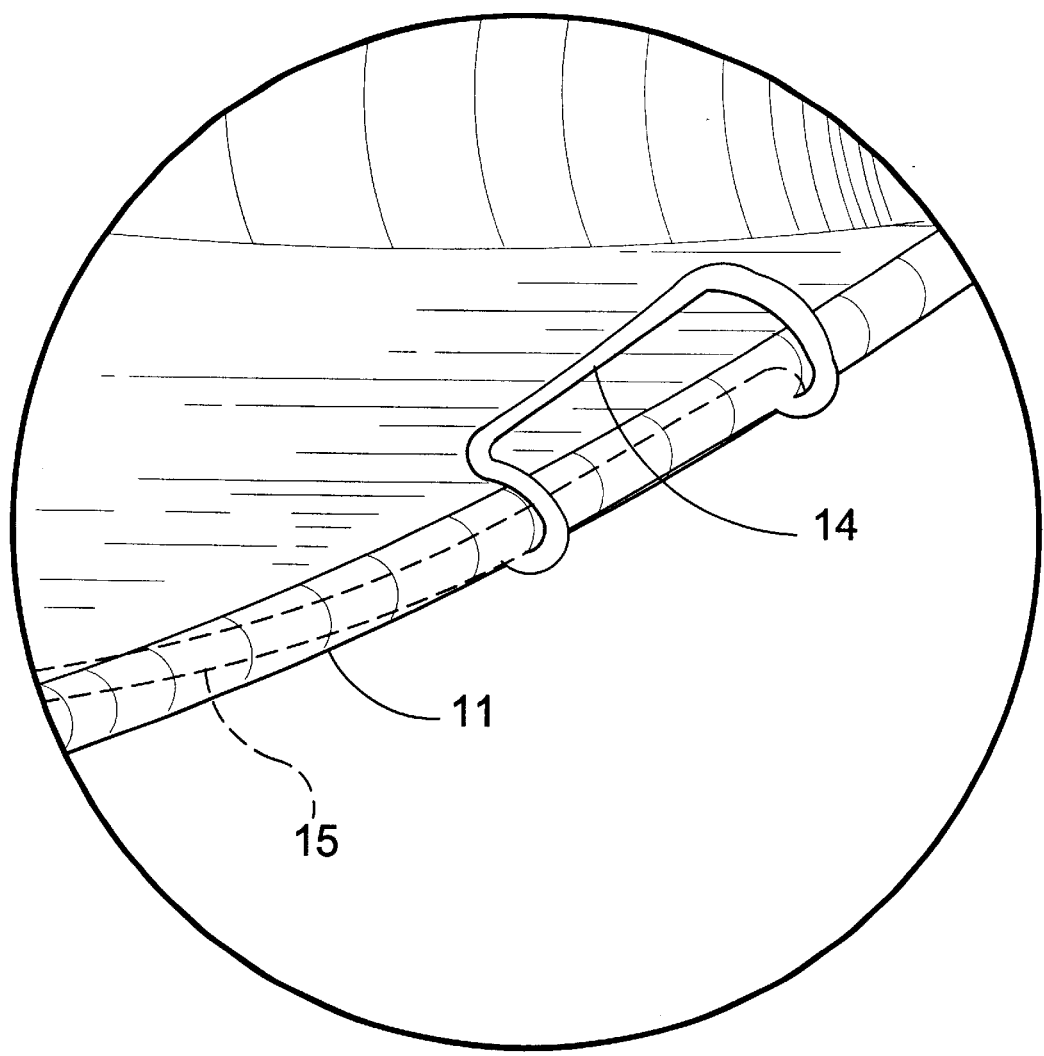
FIG. 11 is a detail view of the left brim clip portion of the present invention mounted on a cap brim.

FIG. 11 is a detail view of the left brim clip 14 mounted on cap brim 11. Left brim clip 14 attaches wire frame 15 of the AGSA to the underside of brim 11 of a cap or brimmed hat. Thus AGSA attaches to the brim of a cap or hat via left brim clip 14 and right brim clip 13 (not shown). The brim clips hold the adjustable glare shield assembly (AGSA) to the brim of the hat firmly and can be removed and replaced as desired by the user. The clips at the ends of the springy wire frame push inward on the brim of the cap.

Although the present invention has been described with reference to preferred embodiments, numerous modifications and variations can be made and still the result will come within the scope of the invention. No limitation with respect to the specific embodiments disclosed herein is intended or should be inferred.

I claim:

1. In combination with a head cover having a brim, said brim extending outward above a user's eyebrows, an improvement comprising:

an arcuate frame having a left and a right end;
    said each end having a clip to fasten to a left and a right portion respectively, of the brim;
    a pivotable bridge assembly mounted centrally on the arcuate frame to allow a user to adjust a tilt of the pivotable bridge assembly;
    an eye shield affixed to the pivotable bridge assembly, thereby providing an eye cover for the user when the pivotable bridge assembly is in a down position; and
    said pivotable bridge assembly comprising a pair of fixed outer washers mounted on the arcuate frame, a pair of clamping arms affixed to said eye shield mounted inside the pair of stationary outer washers for rotation on said arcuate frame, a pair of movable inner washers engaging said clamping arms on sides opposite that of said outer washers, and an inner coil spring surrounding said arcuate frame between the pair of inner washers for acting along a central axis of said arcuate frame for biasing said inner washers against said clamping aims and said outer washer for holding said eye shield in any selected position.

2. The improvement of claim 1, wherein the eye shield further comprises a left and a right lens.

* * * * *